United States Patent [19]
Shashoua

[11] Patent Number: 6,153,653
[45] Date of Patent: Nov. 28, 2000

[54] CHOLINE COMPOSITIONS AND USES THEREOF

[75] Inventor: Victor E. Shashoua, Belmont, Mass.

[73] Assignee: Protarga, Inc., Conshohocken, Pa.

[21] Appl. No.: 08/979,313

[22] Filed: Nov. 26, 1997

[51] Int. Cl.[7] .................................................. A61K 31/14
[52] U.S. Cl. ............................................................ 514/642
[58] Field of Search ............................................. 514/642

[56] References Cited

U.S. PATENT DOCUMENTS

| | | | |
|---|---|---|---|
| 4,692,441 | 9/1987 | Alexander et al. | 514/194 |
| 4,729,989 | 3/1988 | Alexander et al. | 514/192 |
| 4,939,174 | 7/1990 | Shashoua | 514/549 |
| 5,112,863 | 5/1992 | Hashimoto et al. | 514/534 |
| 5,214,062 | 5/1993 | Mark et al. | 514/369 |
| 5,223,263 | 6/1993 | Hostetler et al. | 424/450 |
| 5,308,832 | 5/1994 | Garleb et al. | 514/2 |
| 5,411,947 | 5/1995 | Hostetler et al. | 514/43 |
| 5,466,841 | 11/1995 | Horrobin et al. | 554/79 |
| 5,516,800 | 5/1996 | Horrobin | 514/560 |
| 5,604,198 | 2/1997 | Poduslo et al. | 514/6 |
| 5,604,216 | 2/1997 | Horrobin | 514/182 |
| 5,646,180 | 7/1997 | Chaturvedi | 514/471 |
| 5,654,290 | 8/1997 | Bayon et al. | 514/77 |
| 5,795,909 | 8/1998 | Shashoua et al. | 514/449 |

FOREIGN PATENT DOCUMENTS

| | | |
|---|---|---|
| 693498 | 1/1996 | European Pat. Off. . |
| 6072868 | 3/1994 | Japan . |
| 7082146 | 3/1996 | Japan . |
| 8151334 | 6/1996 | Japan . |
| 9030963 | 2/1997 | Japan . |
| WO96/12696 | 5/1996 | WIPO . |
| WO96/27380 | 9/1996 | WIPO . |

OTHER PUBLICATIONS

Schabitz WR, et al., "The Effects of Prolonged Treatment With Citicoline in Temporary Experimental Focal Ischemia", *J Neurol Sci,* 1996, 138(1–2); 21–25. (Abstract).

D'Orlando KJ, et al., "Citicoline (CDP–Choline): Mechanisms of Action and Effects in Ischemic Brain Injury", *Neurol Res,* 1995, 17(4): 281–284. Review.

Nishio K, et al., "Novel Water–Soluble Derivatives of Docosahexaenoic Acid Increase Diacyl–Glycerol Production Mediated by Phosphatidylcholine–Specific Phospholipase C", *Proc Soc Exp Biol Med,* 1993, 203(2): 200–208.

Nishio, K. et al., DHA–Vc, DHA–cho, and PC Metabolism: 200–208 (1993).

*Primary Examiner*—Phyllis G. Spivack
*Attorney, Agent, or Firm*—Wolf, Greenfield & Sacks, PC

[57] ABSTRACT

The invention provides compositions that include conjugates of choline and a fatty acid, preferably cis-docosahexaenoic acid. The conjugates are useful in treating disorders resulting from cerebral ischemia including stroke.

18 Claims, 1 Drawing Sheet

* $p < 0.05$ Compared with 0 dose

CHOLINE COMPOSITIONS AND USES THEREOF

BACKGROUND OF THE INVENTION

Stroke is a condition resulting from cerebral ischemia, i.e. a reduction or blockage of blood flow to the brain, which has neurodegenerative effects. About 500,000 Americans suffer strokes each year, 80% of which are caused by a blood clot blocking one of the cerebral blood vessels. Symptoms of stroke include weakness, numbness or paralysis of the face, arm or leg; sudden loss or dimness of vision; loss of speech or difficulty using or understanding language; sudden, severe unexplained headache; or unexplained dizziness, unsteadiness or sudden falls (particularly if associated with one of the above symptoms).

Medications that protect neurons which are at risk following stroke are useful in reducing the neurodegenerative aspects of stroke. Treatments which can be administered after a stroke are particularly desirable since it cannot be predicted when onset of stroke will occur. Protection of the neurons from further degeneration permits treatment to restore normal blood flow to the brain (e.g., using thrombolytics to dissolve blood clots or surgery to repair a leaking blood vessel) prior to irreversible debilitating neuronal damage.

Cytidine 5'-diphosphocholine (CDP-choline, citicholine) is an example of a neuroprotective medication which can exert protective effect when administered after a stroke. Cytidine 5'-diphosphocholine is a natural precursor of phospholipids such as phosphatidylcholine; when cytidine 5'-diphosphocholine is administered, choline and cytidine are released into the systemic circulation. These molecules cross the blood-brain barrier and are incorporated in membrane phospholipids. CDP-choline has been shown to have a neuroprotective effect in animal models and in clinical trials, and improves memory and learning deficits in models of aging. Thus CDP-choline appears suitable for treatment of conditions resulting from cerebral ischemia, such as stroke, and neurodegenerative disorders involving loss of cognition, such as Alzheimer's disease.

Fatty acids previously have been conjugated with drugs to help the drugs as conjugates cross the blood-brain barrier. For example, DHA (docosahexaenoic acid) is a 22 carbon naturally-occurring, unbranched fatty acid that previously has been shown to be unusually effective in crossing the blood-brain barrier. When DHA is conjugated to a drug, the entire drug-DHA conjugate is transported across the blood-brain barrier and into the brain.

DHA is attached via the acid group to hydrophilic drugs and renders these drugs more hydrophobic (lipophilic). DHA is an important constituent of the brain and recently has been approved as an additive to infant formula. It is present in the milk of lactating women. The mechanism of action by which DHA helps drugs conjugated to it cross the blood-brain barrier is unknown.

Another example of the conjugation of fatty acids to a drug is the attachment of pipotiazine to stearic acid, palmitic acid, enanthic acid, undecylenic acid or 2,2-dimethyl-palmitic acid. Pipotiazine is a drug that acts within the central nervous system. The purpose of conjugating pipotiazine to the fatty acids was to create an oily solution of the drug as a liquid implant for slow release of the drug when injected intramuscularly. The release of the drug appeared to depend on the particular fatty acid selected, and the drug was tested for its activity in the central nervous system.

Lipidic molecules, including the fatty acids, also have been conjugated with drugs to render the conjugates more lipophilic than the drug. In general, increased lipophilicity has been suggested as a mechanism for enhancing intestinal uptake of drugs into the lymphatic system, thereby enhancing the entry of the conjugate into the brain and also thereby avoiding first-pass metabolism of the conjugate in the liver. The type of lipidic molecules employed have included phospholipids, non-naturally occurring branched and unbranched fatty acids, and naturally occurring branched and unbranched fatty acids ranging from as few as 4 carbon atoms to more than 30 carbon atoms. In one instance, enhanced receptor binding activity was observed (for an adenosine receptor agonist), and it was postulated that the pendant lipid molecule interacted with the phospholipid membrane to act as a distal anchor for the receptor ligand in the membrane micro environment of the receptor. This increase in potency, however, was not observed when the same lipid derivatives of adenosine receptor antagonists were used, and generalizations thus were not made possible by those studies.

Conjugates containing choline and fatty acid moieties have been synthesized for various uses. U.S. Pat. No. 5,654,290 describes the preparation of compounds continaing DHA esterified to phosphatidylcholine, lysophosphatidylcholine or a triglyceride. The compounds were found useful for delivering DHA into the brain. Yazawa et al described synthesis of polyunsaturated fatty acid-choline esters, including DHA-choline iodide (JP 05 43,524). Nishio et al. (*Proc. Soc. Exp. Biol. Med.* 203:200–208, 1993) found that choline-docosahexanoate stimulated phosphatidylcholine-specific phospholipase C activity. Another reference (JP 62 45,536) disclosed a variety of fatty acid-choline esters for enhancing oral, nasal and vaginal absorption of pharmaceuticals. U.S. Pat. No. 5,466,841 describes phospholipids containing choline and two different unsaturated fatty acids (one of which can be DHA). None of the foregoing compounds containing choline conjugated to one or more fatty acid moieties have been used in the treatment of stroke or cognitive disorders.

SUMMARY OF THE INVENTION

It has now been discovered that a covalent conjugates of a fatty acid and choline are useful in the treatment of stroke. Unexpectedly, DHA-choline conjugates reduced the effects of cerebral ischemia in an animal model of stroke, even when administered several hours after the ischemic event. Furthermore, DHA-choline conjugates unexpectedly protect cortical neurons selectively following cerebral ischemia. The conjugates are believed useful for thrombotic, embolic, and hemorrhagic stroke.

According to one aspect of the invention, a pharmaceutical composition is provided. A composition contains a covalent conjugate of choline and a fatty acid having 12–26 carbons, in an amount effective to treat stroke, and a pharmaceutically acceptable carrier. Preferably, the fatty acid is an unbranched, naturally occurring fatty acid. More preferably, the fatty acid has 14–22 carbons. It also is preferred that the fatty acid and choline are conjugated via an ester bond between the COOH of the fatty acid and the OH of the choline. Unbranched common naturally occurring fatty acids include C12:0 (lauric acid), C14:0 (myristic acid), C16:0 (palmitic acid), C16:1 (palmitoleic acid), C16:2, C18:0 (stearic acid), C18:1 (oleic acid), C18:1-7 (vaccenic), C18:2-6 (linoleic acid), C18:3-3 (α-linolenic acid), C18:3-5 (eleostearic), C18:3-6 (β-linolenic acid), C18:4-3, C20:1 (gondoic acid), C20:2-6, C20:3-6 (dihomo-y-linolenic acid), C20:4-3, C20:4-6 (arachidonic acid) C20:5-3 (eicosapentaenoic acid), C22:1 (docosenoic acid), C22:4-6 (docosatetraenoic acid), C22:5-6 (docosapentaenoic acid), C22:5-3 (docosapentaenoic ), C22:6-3 (docosahexaenoic acid) and C24:1-9 (nervonic). Highly preferred unbranched, naturally occurring fatty acids are those with between 14 and 22 carbon atoms. The most preferred fatty acid is docosahexaenoic acid. Most preferably, the composition is

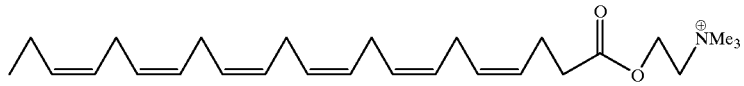

The pharmaceutical composition further can comprise an anti-stroke agent other than the covalent conjugate. In certain embodiments, the anti-stroke agent is selected from the group consisting of antiplatelet agents, anticoagulation agents, thrombolytic agents including plasminogen activators, antithrombotics, neuroprotective agents, platelet activating factor antagonists, platelet aggregation inhibitors, post-stroke and post-head trauma treatments, cerebral ischemia agents, basic fibroblast growth factors and steroids. Most preferably, the anti-stroke agent is selected from the group consisting of citicholine, dizocilpine, urokinase tissue plasminogen activation and lexipafant.

According to another aspect of the invention, a kit is provided. The kit is a package which houses a container which contains the covalent conjugate of the invention and also houses instructions for administering the covalent conjugate to a stroke victim.

According to another aspect of the invention, a second kit is provided. This kit includes a package which houses a first container which contains the covalent conjugate of the invention and also houses a second container containing an anti-stroke agent other than the covalent conjugate.

In the kits of the invention, the preferred fatty acids, bonds, covalent conjugate and anti-stroke agent other than the covalent conjugate are as described above.

According to another aspect of the invention, a method is provided for treating stroke. The method involves administering to a subject in need of such treatment a covalent conjugate of choline and a fatty acid having 12–26 carbons in an amount effective to treat stroke. The preferred fatty acids, bonds and covalent conjugate are as described above. The method also can involve co-administering to the subject an anti-stroke agent other than the covalent conjugate. Preferred anti-stroke agents are as described above.

According to another aspect of the invention, a method is provided for protecting cortical cells from ischemia-induced cell death. The method involves contacting the cortical cells which have been exposed to ischemic conditions sufficient to induce cell death with a covalent conjugate of choline and a fatty acid having 12–26 carbons in an amount effective to protect the cortical cells against cell death which would otherwise result from the ischemic conditions. Preferred fatty acids, bonds and covalent conjugate are as described above.

According to another aspect of the invention, a method is provided for selectively protecting cortical cells of a subject from stroke-induced cell death. The method involves administering to a subject in need of such treatment a covalent conjugate of choline and a fatty acid having 12–26 carbons in an amount effective to protect the cortical cells from stroke-induced cell death. Preferred fatty acids, bonds and covalent conjugate are as described above. These and other aspects of the invention are described in greater detail below.

DETAILED DESCRIPTION OF THE INVENTION

Figure 1:
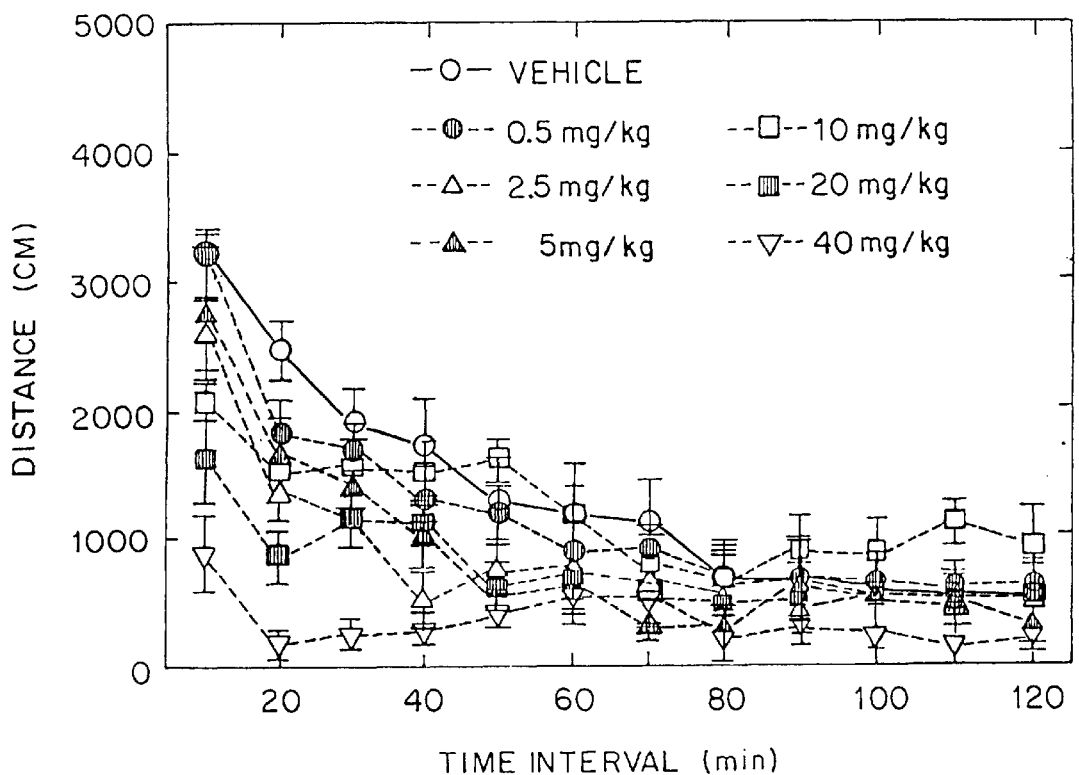
FIG. 1 shows the dose response data for the locomotor activity of mice injected with different doses of DHA-choline, illustrating the time course of effect.
Figure 2:
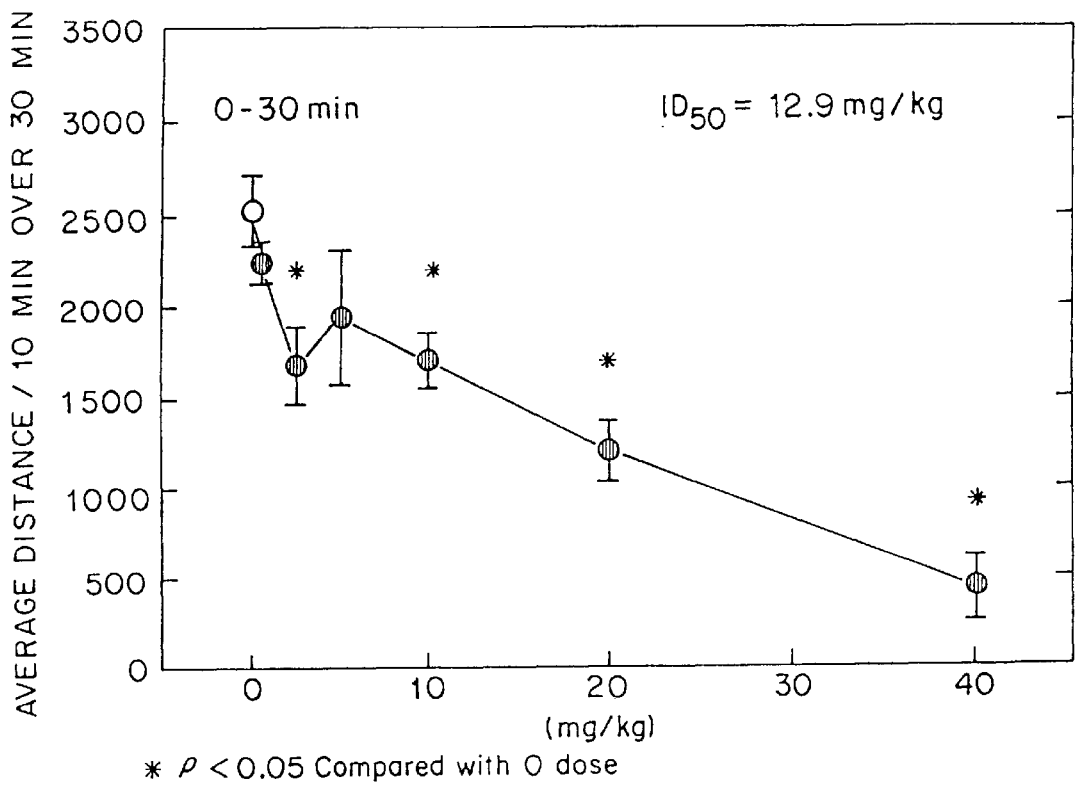
FIG. 2 shows the dose response data for the locomotor activity of mice injected with different doses of DHA-choline, illustrating the dose response 0–30 minutes after 20 minutes pretreatment.

Choline is a naturally occurring alcohol which is a component of lipids (e.g. phosphatidylcholine) and the neurotransmitter acetylcholine. Choline has the following structure:

cis-docosahexaenoic acid (DHA) is a naturally occurring fatty acid. It is an unbranched chain fatty acid with six double bonds, all cis. Its structure is as follows:

DHA can be isolated, for example, from fish oil or can be chemically synthesized. These methods, however, can generate trans isomers, which are difficult and expensive to separate and which may present safety problems in humans. The preferred method of production is biological synthesis to produce the all cis isomer. The preferred source of DHA is from Martek Biosciences Corporation of Columbia, Md. Martek has a patented system for manufacturing DHA using microalgae which synthesize only a single isomer of DHA, the all cis isomer. Martek's patents include U.S. Pat. Nos. 5,374,657, 5,492,938, 5,407,957 and 5,397,591.

DHA also is present in the milk of lactating women, and Martek's licensee has obtained approval in Europe of DHA as a nutritional supplement for infant formula.

It is known that DHA can be unstable in the presence of oxygen. To stabilize DHA and its conjugates it is important to add anti-oxidants to the material after it is synthesized. One method of stabilization is to make-up the newly synthesized material in the following solution: 100 g neat DHA-choline plus 100 g of vehicle (100 ml propylene glycol, 70 mg alpha-tocopherol, 5 mg dialaurylthiodipropionic acid, 50 mg ascorbic acid) prepared and held under argon in amber, sealed vials and stored at four degrees centigrade. The following anti-oxidants may also be employed: ascorbic acid, ascorbyl palmitate, dilauryl ascorbate, hydroquinone, butyated hydroxyanisole, sodium meta bisulfite, t-β carotene and α-tocopherol. A heavy metal chelator such as ethylenediamine tetra-acetic acid (EDTA) may also be used.

In one aspect of the invention, the conjugate is prepared as a quaternary ammonium salt. The anion preferably is selected from the group consisting of I⁻, Cl⁻, OH⁻, F⁻ and Br⁻. Most preferably the anion is I⁻.

In another aspect of the invention, cocktails of the choline-fatty acid conjugate and another anti-stroke agent can be prepared for administeration to subjects having a need for such treatment. One of ordinary skill in the art is familiar with a variety of antistroke agents which are used in the medical arts to treat stroke (thrombotic, embolic and/or hemorrhagic stroke). Such agents include antiplatelet agents, anticoagulation agents, thrombolytic agents including plasminogen activators, antithrombotics, neuroprotective agents, platelet activating factor antagonists, platelet aggregation inhibitors, post-stroke and post-head trauma treatments, cerebral ischemia agents, basic fibroblast growth factors and steroids.

Antiplatelet agents, which inhibit platelet aggregation, include aspirin, ticlopidine and dipyridamole.

Anticoagulation agents reduce or prevent the coagulation of blood components and thus reduce or prevent clot formation; common anticoagulation agents include coumarin and heparin.

Thrombolytic agents function by lysing the clot which causes the thromboembolic stroke. Commonly used thrombolytic agents include urokinase, streptokinase and tissue plasminogen activator (alteplase, tPA). Various modified forms of tPA ("modified tPA") have been characterized and are known to those skilled in the art. Modified tPA includes, but is not limited to, variants having deleted or substituted amino acids or domains, variants conjugated to other molecules, and variants having modified glycosylation. For example, PCT Publication No. W093/24635 discloses tPA variants having an extra glycosylation site at any of the amino acid positions 103–105 and the native glycosylation site removed at position 117 of the native human tPA. The amino acid number refers to the amino acid in that position of the mature, wild-type tPA polypeptide as disclosed in U.S. Pat. No. 4,766,075. The disclosed variants may also include at least one amino acid substituted in the 296–299 position with alanine and/or a substitution of the amino acids at positions 274–277 of wild type tPA (phenylalanine, arginine, isoleucine, lysine) with leucine, histidine, serine, and threonine, respectively. Triple mutants of tPA also are disclosed, including the specific molecule: T103N, N 117Q, KHRR (296–299) AAAA t-PA (TNK t-PA). EP 352,119 discloses vampire bat tPAs (Bat-PAs (H), (I), and (L)). Vampire bat-PAs are variants of native tPA having a variety of sequence modifications. Suzuki et al., (*J. Cardiovasc. Pharmacal.* 22:834–840, 1993) disclose tPA variants in which a cysteine at position 84 of the growth factor domain of native tPA is replaced by serine (C84S tPA). Although this variant retains the functional activity of native tPA, it has been shown to have a longer in vivo half life than native tPA.

Variants of tPA have been developed which retain tPA functionality but have reduced clearance rates. These variants include tPA molecules with deleted amino acids or domains, such as those described by Johannessen et al. (*Throm. Haemostas.* 63:54–59, 1990) and Sobel et al. (*Circulation* 81:1362–73, 1990); tPA molecules which have amino acid substitutions in the regions of 63–72 and 42–49, such as those described by Ahem et al. (*J. Biol. Chem.* 265:5540, 1990); and tPA molecules which have a glutamic acid substituted for the arginine at position 275 of the native t-PA molecule such as that described by Hotchkiss et al. (*Throm. Haemostas.* 55:491, 1987). tPA molecules conjugated to other molecules have also been found to have decreased clearance rates. For example, conjugation of tPA to polyethylene glycol has been shown to reduce the clearance rate of tPA, as disclosed in EP-A304,311. Conjugation of a tPA molecule to a monoclonal antibody has been shown to increase the half-life of tPA in vivo (EP A339,505).

Modification of glycosylation on native tPA has also been found to have an effect on clearance rates of tPA. PCT application WO89/11531 discloses several tPA variants having additional glycosylation sites, which also have decreased clearance rates. Other research has described tPA variants with reduced glycosylation, which also exhibit decreased clearance rates (Martin et al., *Fibrinolysis* 4:9, 1990). Each of the above references is hereby incorporated by reference.

Antithrombotics include anagrelide hydrochloride; bivalirudin; dalteparin sodium; danaparoid sodium; dazoxiben hydrochloride; efegatran sulfate; enoxaparin sodium; ifetroban; ifetroban sodium; tinzaparin sodium; and trifenagrel.

Neuroprotective agents include dizocilpine maleate.

Platelet activating factor antagonists include lexipafant.

Platelet aggregation inhibitors include acadesine; beraprost; beraprost sodium; ciprostene calcium; itazigrel; lifarizine; oxagrelate.

Post-stroke and post-head trauma agents include citicoline sodium.

Cerebral ischemia agents include dextrorphan hydrochloride.

The conjugates of the invention, when used alone or in cocktails, are administered in effective amounts. In general, an effective amount will be that amount necessary to inhibit stroke or the neurodegenerative effects thereof. An effective amount is one sufficient to reduce in vivo brain injury resulting from the stroke. A reduction of brain injury is any prevention of injury to the brain which otherwise would have occurred in a subject experiencing a stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or, in the case of treatment with cocktails, stroke patients treated with antistroke agents alone (i.e. without the conjugate of the invention). These parameters can be monitored using standard diagnostic procedures including magnetic resonance imaging (MRI), computed tomographic (CT) scans, cerebral angiography, noninvasive carotid evaluations by ophthalmodynamometry, oculoplethysmography, range-gated pulsed-Doppler assessment and transcranial Doppler assessment, and the like. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that i.v. doses in the same range will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day are contemplated to achieve appropriate systemic levels of compounds.

When administered, the formulations of the invention are applied in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa.

The invention is used in connection with treating subjects having or suspected of having a stroke. A subject as used herein means humans, primates, horses, cows, pigs, sheep, goats, dogs, cats and rodents.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Intravenous routes are preferred.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

EXAMPLES

Synthesis of DHA-Choline (A) Synthesis of 2-dimethylaminoethyl docosahexaenoate:

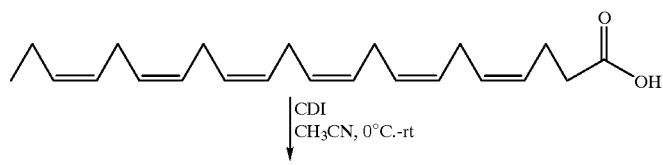

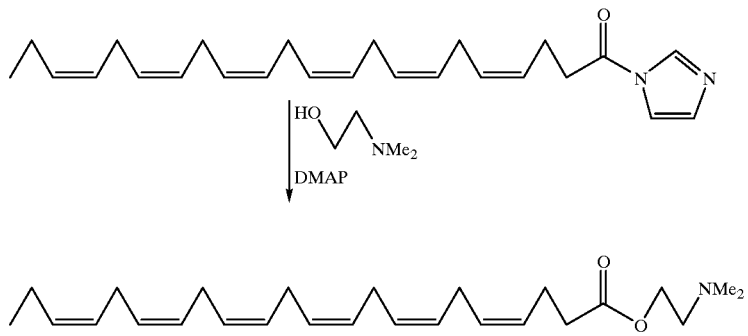

To a solution of docosahexaenoic acid (0.986 g, 3.0 mmol) in CH$_3$CN (6.0 mL) was added carbonyldiimidazole (0.535 g, 3.3 mmol) in one portion at 0° C. The mixture was allowed to warm to room temperature and stirred at room temperature for 30 min. TLC showed a complete reaction (1:1 EtOAc/hexane). N,N-dimethylaminoethanol (0.89 g, 10.0 mmol) was added dropwise followed by addition of 4-dimethylaminopyridine (0.073 g, 0.60 mmol) The mixture was stirred at room temperature overnight. The solvent was removed by rotary evaporation and the residue was purified on silica gel using 72% EtOAc/hexane, 80% EtOAC/hexane and 100% EtOAc with 0.5% MeOH each to provide the product, 2-dimethylaminoethyl docosahexaenoate (1.098 g, 92%), as a light yellow oil. The product was stored at −20° C. with small amount of β-carotene.

(B) Analysis of the product:

(1) TLC:

Rf (100% EtOAc)

DHA choline precursor 0.19

DHA 0.55

N,N-dimethylethanolamine 0.05

Rf (butanol:pyridine:H$_2$O 85:10:5)

DHA choline precursor 0.32

DHA 0.81

N,N-dimethylethanolamine 0.16

(2) Mass spectrum: M$^+$ 400

(3) Elemental analysis: calculated for C$_{26}$H$_{41}$NO$_2$: C % 78.15, H % 8.62, N % 2.92. Found: C % 78.11, H % 10.54, N % 3.42.

(4) NMR:

$^1$H NMR (CDCl$_3$) δ 5.44–5.22 (m, 12 H), 4.13 (t, J=5.75 Hz, 2H), 2.86–2.70 (m, 10 H), 2.52 (t, J=5.75 Hz, 2 H), 2.40–2.30 (m, 4 H), 2.24 (s, 6 H), 2.03 (pent, J=7.50 Hz, 2 H), 0.89 (t, J=7.50 Hz, 3 H).

$^{13}$C NMR (CDCl$_3$) δ 172.65, 131.69, 128.95, 128.25, 127.93, 127.79, 127.64, 127.58, 126.74, 61.84, 57.54, 45.41, 33.83, 25.35, 25.32, 25.26, 22.49, 20.28, 14.01.

(5) Solubility: soluble in EtOAc, Et$_2$O, CH$_2$Cl$_2$, CHCl$_3$, EtOH insoluble in H$_2$O (6) Stability: turns dark when exposed in the air for several days, should be kept at −20° C. under Argon.

(C) Synthesis of Docosahexaenoyl Choline Iodide

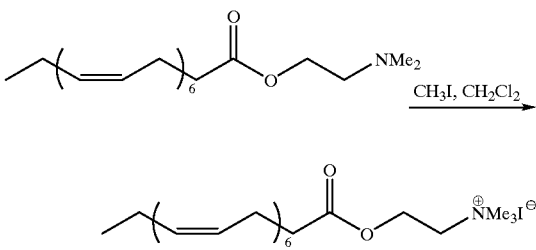

Molecular Formula: C$_{27}$H$_{44}$NO$_2$I; MW: 541.56.

To a solution of 2-dimethylaminoethyl docosahexaenoate (1.12 g, 2.80 mmol) in CH$_2$Cl$_2$ (10.0 mL) was added iodomethane (0.80 g, 5.60 mmol) dropwise at room temperature. The mixture was stirred at room temperature for 3 hr. The solvent and excess reagent was removed under reduced pressure and the residue was triturated with hexanes. The mixture was centrifuged and the supernatant was removed. The residue was dried under reduced pressure to provide the product, docosahexaenoyl choline iodide (1.46 g, 96%), as an off white solid.

(D) Analysis of the product:

(1) Mass spectrum: M$^+$-I 414

(2) NMR $^1$H NMR (CDCl$_3$) δ 5.46–5.21 (m, 12 H), 4.55 (br s, 2 H), 4.11–4.02 (m, 2 H), 3.51 (s, 9 H), 2.86–2.74 (m, 10 H), 2.48–2.30 (m, 4 H), 2.04 (pent, J=7.50 Hz, 2 H), 1.03 (t, J=7.50 Hz, 3 H).

$^{13}$C NMR (CDCl$_3$) δ 171.81, 131.78, 129.51, 128.32, 128.20, 128.05, 127.77, 127.59, 127.16, 126.72, 64.96, 57.56, 54.55, 33.72, 25.37, 25.27, 22.15, 20.30, 14.03.

(3) Solubility: soluble in CH$_2$Cl$_2$, CHCl$_3$, EtOAc, EtOH insoluble in hexanes, Et$_2$O.

5.5 mg dissolved in 1.0 mL ascorbic acid in saline with 0.02 mL detergent 7.8 mg dissolved in 1.0 mL 10% albumin in saline with 0.01 mL detergent (4) Stability: $^1$H NMR analysis of the compound which was exposed in the air for 5 days showed that the compound had not decomposed; however, if it is exposed in the air for too long will decompose. The compound should be kept at −20° C. under Argon. Also purification of the compound on neutral alumina will result in other peaks on $^1$H NMR.

Activity of DHA-Choline (A) Locomotor Activity Studies:

A dose-response study of DHA-choline-induced locomotor depression was conducted using 40 Digiscan locomotor activity testing chambers (40.5×40.5×30.5 cm) housed in sets of two, within sound attenuating chambers. A panel of infrared beams (16 beams) and corresponding photo detectors were located in the horizontal direction along the sides of each activity chamber. A 7.5W incandescent light above each chamber provided dim illumination. Fans provided an 80-dB ambient noise level within the chamber. Separate groups of 8 non-habituated male Swiss-Webster mice (Hsd:ND4, aged 2–3 mo.) were injected via the intraperitoneal route (i.p.) with either vehicle or DHA-choline (0.5, 2.5, 5, 10, 20 or 40 mg/kg), 20 minutes prior to locomotor activity testing. In all studies, the total distance (cm traversed in the horizontal plane) was measured for 2 hours within 10 min periods.

FIG. 1 shows the dose response data for the locomotor activity (Stewart et al., *Psychopharmacol.* 60:281, 1979) of mice injected with different doses of the compound. FIG. 1 shows average distance per 10 min as a function of time (top graph) and dose (bottom graph), 20 minutes following DHA-choline pretreatment. The period 0–30 min was selected for analysis of dose-response data because this is the time period in which DHA-choline produced maximal effects. The mean average distance per 10 min for this 30 min period were fit to a linear function of log, dose of the descending portion of the dose-effect curve (0.5 to 40 mg/kg dose range). The ID$_{50}$ dose producing ½ maximal depressant activity (where maximal depressant activity=0 cm/30 min) was calculated as 12.9 mg/kg.

A one-way analysis of variance conducted on total distance/10 min for the 0–30 time period indicated a significant overall effect $F(6,49)=10.5$, $p<0.001$; planned comparisons (a priori contrast) against the vehicle control showed a significant difference for 2.5, 10, 20 and 40 mg/kg (all ps<0.05 denoted on FIG. 1 with an asterisk).

Thus, these data demonstrate that DHA-choline inhibits locomotor activity in a dose-dependent manner.

(B) Evaluation of DHA-choline as an Anti-stroke Compound

Two sets of experiments were carried out. In the first set, rats were administered with 50 mg/kg of DHA-choline i.p. at 30 minutes prior to occlusion of the middle cerebral artery of the left side of the brain using a standard highly reproducible animal model of stroke (Karpiak et al., *J. Neurosci. Res.* 30:512–520, 1991). Occlusion of the middle cerebral artery inhibits blood flow to a major portion of the left cortical and subcortical regions of the brain. After a two hour period, the occluded blood vessel was opened to allow reperfusion of the brain, and anesthesia was terminated. Each animal received additional doses of 50 mg/kg of DHA-choline 24 and 48 hours later.

At the end of the three days, the animals were tested for neurological deficits and evaluated by the standard test scores of 0 to 5 (0=normal, no deficit; 1=extend forepaw on contralateral side; 2=circling animal; 3=loss of righting reflex; 4=animal cannot stand; 5=dead). All of the vehicle treated rats showed a typical disability to extend the contralateral front paw, and circled on the side of the affected leg while walking. These deficits are primarily associated with cortical damage. All of the drug treated animals did not show paw extension disability and walked normally in a straight line.

The animals were sacrificed, perfused with formalin fixative, brains were sliced into seven 2 mm thick coronal sections, and stained with triphenyltetrazolium chloride (Watson et al., *J. Neurosci. Methods* 53:203–208, 1994). In this test, tissue that contains intact mitochondria stains red, whereas dead tissue with damaged mitochondria picks up no stain and remains white. Each unstained area on the left side of a section was measured and compared to the total area of the control non-occluded right side of the same section of the brain. The area of damaged (white) brain tissue cells was calculated as a percent of the intact right side of a section. Table 1 demonstrates that the number of dead cells decreased by about 50% for the animals treated with DHA-choline. Therefore, DHA-choline rescued brain tissue from effects of occlusion when it is administered at 30 minutes prior to the initiation of ischemia. (n=5 per group.)

In the second set of experiments (n=5), the identical occlusion-reperfusion rat model was used; only the time of administration of the drug was changed. DHA-choline was injected i.p. at a dose of 50 mg/kg at one hour after the beginning of the reperfusion, i.e., at three hours after the initiation of the stroke event. Controls (n=5) received an injection of the vehicle instead of the drug according to the same protocol. Surprisingly, the drug-treated brains showed approximately 50% decrease in the infarct volume, i.e., identical to the results observed in the animals that had received the drug as a pretreatment.

TABLE I

Effect of NMI 96103 on MCA occlusions of rat brain
Infarct volume (% of control non-occluded side of brain)

| Group No. | Vehicle | DHA-choline at 30 min prior to occlusion | DHA-choline at 3 hours after occlusion |
|---|---|---|---|
| 1 | 33 | 22 | 15 |
| 2 | 37 | 19 | 17 |
| 3 | 37 | 16 | 25 |
| 4 | 35 | 20 | 21 |
| 5 | | | 20 |
| Average | 35.5 | 19.3 | 19.6 |

Unexpectedly, there was a complete rescue of the cortical cells in animals that received DHA-choline, regardless of whether DHA-choline was administered prior to the onset of the occlusion or at three hours after the onset of occlusion. All animals treated with DHA-choline had only subcortical infarcts with no incidence of cortical infarcts. These results suggest that DHA-choline is a neuroprotective drug which will be effective for treatment of stroke and which, unexpectedly, completely rescues cortical neurons from death following cerebral ischemia.

Other aspects of the invention will be clear to the skilled artisan and need not be repeated here. All patents, published patent applications and literature cited herein are incorporated by reference in their entirety.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

We claim:

1. A method for treating stroke comprising:
administering to a subject who has experienced a stroke an amount of a covalent conjugate of choline and a fatty acid having 12–26 carbons in an amount effective to treat stroke.

2. The method of claim 1, wherein the fatty acid is an unbranched, naturally occurring fatty acid.

3. The method of claim 2, wherein the fatty acid has 14–22 carbons.

4. The method of claim 1, wherein the fatty acid is conjugated to choline via an ester bond between the COOH of the fatty acid and the OH of choline.

5. The method of claim 1, wherein the covalent conjugate is

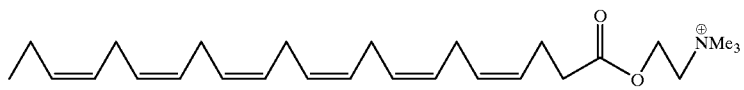

6. The method of claims 1, 2, 3, 4 or 5 further comprising administering to the subject an anti-stroke agent other than the covalent conjugate.

7. The method of claim 6 wherein the anti-stroke agent is selected from the group consisting of antiplatelet agents, anticoagulation agents, thrombolytic agents including plasminogen activators, antithrombotics, neuroprotective agents, platelet activating factor antagonists, platelet aggregation inhibitors, post-stroke and post-head trauma agents, cerebral ischemia agents, basic fibroblast growth factors and steroids.

8. The method of claim 7 wherein the anti-stroke agent is selected from the group consisting of citicholine, dizocilpine, alteplase, urokinase, and lexipafant.

9. A method for protecting cortical cells from ischemia-induced cell death comprising
contacting the cortical cells which have been exposed to ischemic conditions sufficient to induce cell death with a covalent conjugate of choline and a fatty acid having 12–26 carbons in an amount effective to protect the cortical cells against cell death which would otherwise result from the ischemic conditions.

10. The method of claim 9, wherein the fatty acid is an unbranched, naturally occurring fatty acid.

11. The method of claim 10, wherein the fatty acid has 14–22 carbons.

12. The method of claim 9, wherein the fatty acid is conjugated to choline via an ester bond between the COOH of the fatty acid and the OH of choline.

13. The method of claim 9, wherein the covalent conjugate is

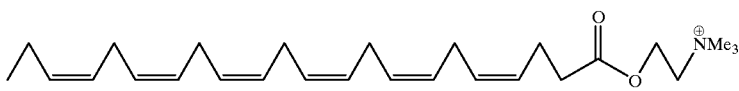

14. A method for selectively protecting cortical cells of a subject from stroke-induced cell death comprising:
administering to a subject who has experienced a stroke a covalent conjugate of choline and a fatty acid having 12–26 carbons in an amount effective to protect the cortical cells from stroke-induced cell death.

15. The method of claim 14, wherein the fatty acid is an unbranched, naturally occurring fatty acid.

16. The method of claim 15, wherein the fatty acid has 14–22 carbons.

17. The method of claim 14, wherein the fatty acid is conjugated to choline via an ester bond between the COOH of the fatty acid and the OH of choline.

18. The method of claim 14, wherein the covalent conjugate is

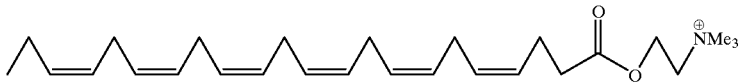

* * * * *